US006380437B1

(12) United States Patent
Shi et al.

(10) Patent No.: US 6,380,437 B1
(45) Date of Patent: Apr. 30, 2002

(54) PROCESS FOR THE PREPARATION OF UNSATURATED 4,5-ALLENE KETONES, 3,5-DIENE KETONES AND THE CORRESPONDING SATURATED KETONES

(75) Inventors: Nongyuan Shi, Hainburg (DE); Frank Hübner, Mobile, AL (US); Bernd Drapal, Alzenau (DE); Rainer Peter, Krombach (DE); Steffen Krill, Speyer (DE); Klaus Huthmacher, Gelnhausen (DE); Christoph Weckenbecker, Gründau-Lieblos (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 09/685,933

(22) Filed: Oct. 11, 2000

(30) Foreign Application Priority Data

Oct. 15, 1999 (DE) .......................................... 199 49 796

(51) Int. Cl.$^7$ ............................................ C07C 49/203
(52) U.S. Cl. ........................ 568/405; 568/383; 568/409
(58) Field of Search ................................ 568/309, 310, 568/322, 323, 341, 361, 364, 384, 383, 386, 403, 404, 405, 407, 408, 409

(56) References Cited

U.S. PATENT DOCUMENTS 3,029,287 A    4/1962   Marbet et al.

FOREIGN PATENT DOCUMENTS

DE    1215694    5/1966
DE    1230783    12/1966

OTHER PUBLICATIONS

Sul'man et al, Khim–Farm. Zh., 24(10), 76–8 (1990) —Abstract only.*

\* cited by examiner

*Primary Examiner*—Sreeni Padmanabhan
(74) *Attorney, Agent, or Firm*—Smith, Gambrell & Russell, LLP

(57) ABSTRACT

Process for the preparation of unsaturated 4,5-allene ketones by reaction of tertiary propargyl alcohols with alkenyl alkyl ethers or ketals in the presence of aliphatic sulfonic acids or sulfonic acid salts.

9 Claims, No Drawings

PROCESS FOR THE PREPARATION OF UNSATURATED 4,5-ALLENE KETONES, 3,5-DIENE KETONES AND THE CORRESPONDING SATURATED KETONES

INTRODUCTION AND BACKGROUND

The present invention relates to a new process for the preparation of 4,5-allene ketones by the Saucy-Marbet reaction by reacting tertiary propargyl alcohols with alkenyl ethers in the presence of aliphatic sulfonic acids or sulfonic acid salts. The 4,5-allene ketones formed as a result can be converted in a manner known per se into 3,5-diene ketones by a subsequent isomerization or into saturated ketones by a subsequent hydrogenation. A number of 4,5-allene ketones, 3,5-dienones and the corresponding saturated ketones are valuable intermediate products for the preparation of vitamin E, A, $K_1$ and carotenoids.

A process for the preparation of 4,5-allene ketones by reaction of propargyl alcohols with alkenyl ethers in the presence of an acid catalyst is described in U.S. Pat. No. 3,029,287 and from the publication by R. Marbet and G. Saucy, Helv. Chim. Acta (1967), 50, 1158–1167. p-Toluenesulfonic acid is mentioned in these as a particularly suitable acid catalyst. However, the reaction times necessary to achieve a complete conversion of the tertiary propargyl alcohol are longer than 15 hours. In an industrial process, these long reaction times cause large reaction volumes and high investment costs.

According to EP 0 902 001 A1, 4,5-allene ketones are prepared by reaction of propargyl alcohols with alkenyl ethers at elevated temperature and pressure in the presence of $KHSO_4$, ketals being formed. The resulting ketal can be recycled back into the alkenyl ether. For this reaction with propine or allene or mixtures thereof in the gas phase at elevated temperature, a heterogeneous catalyst comprising a zinc silicate which is amorphous to X-rays is necessary, which limits the profitability of the process.

Accordingly, an object of the present invention is to improve the space-time yield in the reaction between tertiary propargyl alcohols with alkenyl ethers and thereby achieving good yields.

SUMMARY OF THE INVENTION

It has now been found that aliphatic sulfonic acids and sulfonic acid salts catalyze the reaction of tertiary propargyl alcohols with alkenyl ethers very selectively, the reaction times for achieving good yields being shortened.

The above and other objects of the invention can be achieved by a process for the preparation of 4,5-allene ketones of the formula I

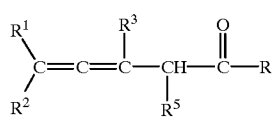

In which
R$^1$ and R$^2$ represent hydrogen, saturated or unsaturated, branched or unbranched $C_1$ to $C_{20}$- alkyl, aryl or alkylaryl, it also being possible for R$^1$ and R$^2$ together to form a 5- or 6-membered ring,
R$^3$ and R$^5$ represent hydrogen or $C_1$ to $C_4$-alkyl and
R$^4$ represents $C_1$ to $C_4$ alkyl, by reacting a tertiary propargyl alcohol of the formula II

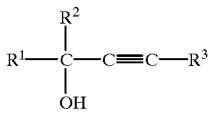

in which R$^1$, R$^2$ and R$^3$ have the abovementioned meaning, with an alkenyl alkyl ether of the formula III

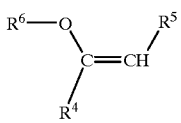

in which R$^4$, R$^5$ have the abovementioned meaning, R$^6$ represents $C_1$ to $C_4$ alkyl
or a ketal of the form IV

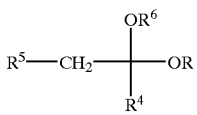

in which
R$^4$, R$^5$ and R$^6$ have the abovementioned meaning, at temperatures of 40 to 200° C. without a solvent or in an inert organic solvent in the atmosphere or under a pressure of up to 100 bar in the presence of an aliphatic sulfonic acid of the formula V

    V in which
R$^7$ represents halogen, branched or unbranched, optionally halogen-substituted alkyl having 1 to 20 C atoms or cycloalkyl,
or in the presence of a sulfonic acid salt of the formula VI

    VI in which
R$^8$=R$^7$ and additionally represents aryl or substituted aryl and
M represents a cation of an organic or inorganic base.
Preferred starting materials of the formula II are, above all, tertiary propargyl alcohols, wherein preferably
R$^1$ represents a saturated or unsaturated, branched or unbranched $C_1$ to $C_{20}$- alkyl, aryl, or arylalkyl,
R$^2$ represents $C_1$ to $C_4$ alkyl, in particular methyl.
Examples of suitable propargyl alcohols which may be mentioned are:
3-methyl-1-butyn-3-ol,
3,7-dimethyl-6-octen-1-yn-3-ol (dehydrolinalool)
3,7-dimethyl-5-octen-1-yn-3-ol
3,7-dimethyl-4-octen-1-yn-3-ol
3,7-dimethyl-1-octyn-3-ol (hydrodehydrolinalool)
3,7,11-trimethyl-6,10-dodecadien-1-yn-3-ol (dehydronerolidol)
3,7,11-trimethyl-6-dodecen-1-yn-3-ol
3,7,11-trimethyl-1-dodecyn-3-ol (hydrodehydronerolidol)
1-ethynyl-1-cyclohexanol, 1-ethynyl-2,2,6-trimethyl-1-cyclohexanol Possible alkenyl alkyl ethers of the formula III are preferably compounds in which $R^4$ represents hydrogen or methyl, $R^5$ represents hydrogen or methyl, $R^6$ represents methyl, ethyl, propyl, isopropyl, isobutyl or tert-butyl.

Examples of suitable alkenyl ethers which may be mentioned are:

isopropenyl methyl ether, isopropenyl ethyl ether, isopropenyl propyl ether, isopropenyl butyl ether, isopropenyl isobutyl ether, isobutyl isopropenyl ether, diisopropenyl ether, isopropenyl phenyl ether, 2-methoxy-1-butene, 2-ethoxy-1-butene, 2-propoxy-1-butene, 3-butoxy-1-butene, 2-methoxy-2-butene, 2-ethoxy-2-butene, 2-methoxy-1-pentene, 2-ethoxy-1-pentene, 2-methoxy-2-pentene, 2-ethoxy-2-pentene, 3-methoxy-3-pentene, 3-ethoxy-2-pentene, in particular isopropenyl methyl ether, isopropenyl ethyl ether and isopropenyl isopropyl ether.

Examples of suitable aliphatic sulfonic acids which may be mentioned are:

methanesulfonic acid, ethanesulfonic acid, propanesulfonic acid, butanesulfonic acid, pentanesulfonic acid, hexanesulfonic acid, halogen-substituted methanesulfonic acid, fluorosulfonic acid and cyclohexanesulfonic acid, in particular methane- and ethanesulfonic acid.

Examples of suitable sulfonic acid salts which may be mentioned are:

pyridinium p-toluenesulfonate, tetramethylammonium p-toluenesulfonate, pyridinium methanesulfonate, pyridinium ethanesulfonate, in particular pyridinium p-toluenesulfonate.

The sulfonic acids and the sulfonic acid salts mentioned can be either employed directly or prepared in situ via the corresponding sulfonic acid chlorides or anhydrides in a known manner.

The reaction is expediently carried out at temperatures between about 40° C. and 200° C., preferably between about 50° C. and 120° C.

The reaction can be carried out under normal pressure, but also under pressure. In a reaction under pressure, the reaction takes place in a pressure range from 1 to 100 bar, preferably 1 to 20 bar. The process can also be carried out as follows: In a 1st stage in the atmosphere and then the 2nd stage under increased pressure.

The molar ratio between the tertiary alcohol of the general formula II and the alkenyl alkyl ether of the general formula III in the process according to the invention is in general between 1:2 to 1:10, preferably between 1:2 to 1:3. In a reaction without a solvent, the excess alkenyl alkyl ether serves as the solvent and can be recovered by distillation when the reaction has ended.

The Saucy-Marbet reaction can be carried out with or without a solvent. Suitable solvents which can be employed in the context of the present invention are hydrocarbons, e.g. hexane, heptane, octane, toluene, and xylene, or ketones and ethers, e.g. isobutyl methyl ketone, diethyl ketone, isophorone or dimethoxypropane.

For carrying out the process, a procedure is in general followed in which either a mixture of the tertiary propargyl alcohol and the alkenyl alkyl ether is initially introduced into the reaction vessel and the catalyst is added either continuously or in portions in the form of a solid, a melt or, in particular, as a solution in a suitable solvent. Thereafter, the mixture is heated up to the reaction temperature. The acid catalyst can be initially introduced with the reactants or metered into the mixture in portions during the reaction.

The reaction can be carried out discontinuously, but also continuously.

The product formed, the 4,5-allene ketone, can be either isolated directly or converted by basic isomerization in a manner known per se (see U.S. Pat. No. 3,029,287) into a 3,5-dienone of the general form

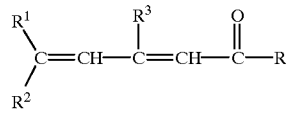

VII in which $R^1$, $R^2$, $R^3$ and $R^4$ have the abovementioned meaning;

the latter can be used as important intermediate stages for vitamin A, E, $K_1$ and carotenoids.

However, the 4,5-allene ketones formed can also be hydrogenated in a manner known per se (R. Marbet and G. Saucy, Helv. Chim. Acta (1967),50; 1158–1167) to give saturated ketones

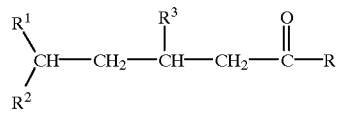

VIII in which $R^1$, $R^2$, $R^3$ and $R^4$ have the abovementioned meaning.

The saturated ketones can be important intermediate products for vitamin E synthesis.

DETAILED DESCRIPTION OF THE INVENTION

The following examples illustrate the invention. The propargyl alcohols employed are described in U.S. Pat. No. 3,029,287 which is relied on and incorporated herein by reference.

EXAMPLE 1

30.5 g 3,7-dimethyl-1-octin-6-en-3-ol, 28.9 g isopropenyl methyl ether and 60 ml n-heptane were initially introduced into a 250 ml flask and 7.7 mg methanesulfonic acid were then added. The reaction mixture was stirred under reflux for 7.5 hours. During this period of time, it was topped up with 14.4 g isopropenyl methyl ether and 11.6 mg methanesulfonic acid in two portions. After cooling, it was neutralized with 2 ml methanolic NaOAc solution (10 g/1) and evaporated. The crude allene ketone obtained was hydrogenated to tetrahydrogeranylacetone in 2-propanol with 10% Pd/A-charcoal. The overall yield of tetrahydrogeranylacetone was 90%.

EXAMPLE 2

30.5 g 3,7-dimethyl-1-octin-6-en-3-ol, 36 g isopropenyl methyl ether and 60 ml n-heptane were initially introduced into a 250 ml flask and 22 mg ethanesulfonic acid were then added. The reaction mixture was stirred under reflux for 7 hours. During this period of time, it was topped up with 7.3 g isopropenyl methyl ether and 4.4 mg ethanesulfonic acid. After cooling to room temperature, it was neutralized with 2 ml methanolic NaOAc solution (10 g/1) and evaporated. The crude allene ketone obtained was hydrogenated to tetrahydrogeranylacetone in 2-propanol with 10% Pd/A-charcoal. Tetrahydrogeranylacetone was obtained in a yield of 88%.

EXAMPLE 3

30.5 g 3,7-dimethyl-1-octin-6-en-3-ol, 28.9 g isopropenyl methyl ether and 60 ml n-heptane were initially introduced into a 250 ml flask and 25 mg pyridinium toluene-4-sulfonate were then added. The reaction mixture was stirred under reflux for 7.5 hours. During this period of time, it was topped up with 14.4 g isopropenyl methyl ether and 50 mg pyridinium toluene-4-sulfonate in two portions. After cooling, the reaction mixture was neutralized with 2.5 ml methanolic NaOAc solution (10 g/l) and evaporated. The crude allene ketone obtained was hydrogenated to tetrahydrogeranylacetone in 2-propanol with 10% Pd/A-charcoal. The overall yield of tetrahydrogeranylacetone was 90%.

EXAMPLE 4

60.9 g 3,7-dimethyl-6-octen-1-in-3-ol, 46.2 g isopropenyl methyl ether and 160 mL n-heptane were initially introduced into a 500 ml flask under nitrogen. 23 mg methanesulfonic acid were added, while stirring. The reaction mixture was stirred under reflux for 6 hours. During this period of time, 56.3 g isopropenyl methyl ether were added in two portions and 44.3 mg methanesulfonic acid were added in 3 portions. The mixture was cooled to room temperature and neutralized by addition of 5.75 mL of a methanolic NaOAc solution (10 mg/mL). The reaction mixture was evaporated. For the rearrangement, the allene ketone crude product obtained was added to a mixture of 40 mL methanol and 0.5 mL 30% sodium hydroxide solution at 0 to 10° C., with vigorous stirring. 40 mL n-heptane were also added to the mixture. After addition of 0.3 mL glacial acetic acid, the mixture was warmed to room temperature and evaporated. The residue was taken up in 150 mL n-hexane and the mixture was washed with water. The organic phase was dried with magnesium sulfate and evaporated. After distillation in vacuo, 72.8 g pseudoionone were obtained, corresponding to a yield of 92%.

EXAMPLE 5

The experiment was carried out analogously to example 4, 176 mg pyridinium toluene-4-sulfonate being employed as the catalyst instead of methanesulfonic acid. After rearrangement, working up and distillation, 71.1 g pseudoionone were obtained, corresponding to a yield of 92%.

EXAMPLE 6

30.9 g 3,7-dimethyl-1-octin-3-ol, 28.9 g isopropenyl methyl ether and 60 ml n-heptane were initially introduced into a 250 ml flask and 7.7 mg methanesulfonic acid were then added. The reaction mixture was stirred under reflux for 7.7 hours. During this period of time, it was topped up with 14.4 g isopropenyl methyl ether and 7.7 mg methanesulfonic acid. The mixture was cooled, neutralized with 1.5 ml methanolic NaOAc solution (10 g/l) and evaporated. The allene ketone crude product obtained was hydrogenated to tetrahydrogeranylacetone in 2-propanol with 10% Pd/A-charcoal. The overall yield of tetrahydrogeranylacetone was 89%.

EXAMPLE 7

The experiment was carried out analogously to example 6, 75 mg pyridinium toluene-4-sulfonate being employed as the catalyst instead of methanesulfonic acid. After hydrogenation and working up, tetrahydrogeranylacetone was obtained in an overall yield of 90%.

EXAMPLE 8

30.9 g 3,7-dimethyl-1-octin-3-ol, 28.9 g isopropenyl methyl ether and 60 ml n-heptane were initially introduced into a 250 ml flask and 25 mg pyridinium toluene-4-sulfonate were then added. The reaction mixture was stirred under reflux for 7 hours. During this period of time, 14.4 g isopropenyl methyl ether and 25 mg pyridinium toluene-4-sulfonate were added in two portions. When the reaction had ended, the solution was evaporated. The residue was distilled in vacuo. 31.9 g 6,10-dimethyl-4,5-undecadien-2-one were obtained, which corresponds to a yield of 82%.

EXAMPLE 9

21.1 g 2-methyl-3-butin-2-ol, 54.1 g isopropenyl methyl ether, 0.05 g hydroquinone and 100 mL n-heptane were initially introduced into a 500 ml flask. 20.7 mg methanesulfonic acid were added, while stirring. The reaction mixture was stirred under reflux for 6.5 hours. After cooling, it was neutralized with 2 ml methanolic NaOAc solution (10 g/l) and evaporated. After distillation in vacuo, 27.5 g 6-methyl-4,5-heptadien-2-one were obtained, corresponding to a yield of 89%.

EXAMPLE 10

The experiment was carried out analogously to example 9, 56.6 mg pyridinium toluene-4-sulfonate being employed as the catalyst instead of methanesulfonic acid. The yield of 6-methyl-4,5-heptadien-2-one was 91%.

EXAMPLE 11

56.1 g 3,7,11-trimethyl-1-dodecin-3-ol, 27.0 g isopropenyl methyl ether and 100 mL n-heptane were initially introduced into a 500 ml flask. 14.5 mg methanesulfonic acid were added, while stirring. The reaction mixture was stirred under reflux for 7.5 hours. During this period of time, 36.5 g isopropenyl methyl ether and 21.6 mg methanesulfonic acid were added in each case in two portions. The mixture was cooled to room temperature, neutralized with 3 ml methanolic NaOAc solution (10 g/l) and evaporated. The crude was hydrogenated with 10% Pd/C in isopropanol. Phytone was obtained in a yield of 91%.

EXAMPLE 12

The experiment was carried out analogously to example 11, 94.2 mg pyridinium toluene-4-sulfonate being employed as the catalyst in 3 portions instead of methanesulfonic acid. After working up and hydrogenation, phytone was obtained in a yield of 91%.

EXAMPLE 13

The experiment was carried out analogously to example 11, 41.3 mg ethanesulfonic acid being added as the catalyst in 3 portions instead of methanesulfonic acid. After working up and hydrogenation, phytone was obtained in a yield of 91%.

EXAMPLE 14

44.9 g 3,7,11-trimethyl-1-dodecin-3-ol and 50.5 g isopropenyl methyl ether were initially introduced into a 300 ml V4A steel autoclave with a temperature probe, sampler and pressure indicator. 19 mg methanesulfonic acid were added, while stirring. The autoclave was forced up to 2 bar with nitrogen. The mixture was stirred at 90 to 95° C. for 8 hours. After cooling, the reaction mixture was neutralized with 1.7 ml methanolic NaOAc solution (10 g/l). After evaporation, the crude product was hydrogenated in 2-propanol with 10% Pd/A-charcoal. Phytone was obtained in a yield of 87%.

EXAMPLE 15

44.1 g 3,7,11-trimethyl-6,10-dodecadien-1-in-3-ol, 50.5 g isopropenyl methyl ether and 80 mL n-heptane were initially introduced into a 500 ml flask. 29 mg methanesulfonic acid were added, while stirring. The reaction mixture was stirred under reflux for 6 hours. After the end of the reaction, the mixture was cooled to room temperature, neutralized with 2.5 ml methanolic NaOAc solution (10 g/l) and evaporated. The residue was hydrogenated in 2-propanol with 10% Pd/A-charcoal. Phytone was obtained in a yield of 76%.

EXAMPLE 16

The experiment was carried out analogously to example 15, 33 mg ethanesulfonic acid being employed as the catalyst instead of methanesulfonic acid. Phytone was obtained in a yield of 73%.

EXAMPLE 17

25.3 g 2-methyl-3-butin-2-ol, 65.0 g isopropenyl methyl ether, 0.066 g hydroquinone and 120 ml n-heptane were initially introduced into a 500 ml flask under nitrogen. 15.0 mg fluorosulfonic acid were added, while stirring. The mixture was heated to the boiling point and stirred under reflux at 60 to 77° C. for 9 h. After cooling, it was neutralized with 2 ml methanolic NaOAc solution (10 g/l) and evaporated. After distillation, 32.7 g 6-methyl-4,5-heptadien-2-one were obtained, which corresponds to a yield of 87.86.

Further variations and modifications will be apparent to those skilled in the art from the foregoing and are intended to be encompassed by the claims appended hereto.

German priority application 199 49 796.8 is relied on and incorporated herein by reference.

We claim:

1. Process for the preparation of an unsaturated 4,5-allene ketone, of the general formula I

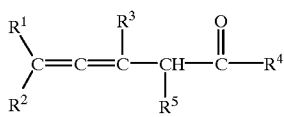

in which
R$^1$ and R$^2$ represent a hydrogen, saturated or unsaturated, branched or unbranched C$_1$ to C$_{20}$-alkyl, aryl or alkylaryl, and R$^1$ and R$^2$ together form a 5- or 6-membered ring,
R$^3$ and R$^5$ represent hydrogen or a C$_1$ to C$_4$-alkyl and
R$^4$ represents a C$_1$ to C$_4$ alkyl,
by reacting a tertiary propargyl alcohol of the general formula II

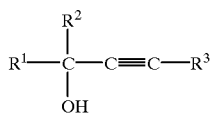

in which R$^1$, R$^2$ and R$^3$ have the abovementioned meaning, with an alkenyl alkyl ether of the general formula III

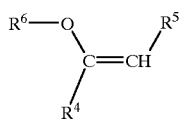

in which R$^4$, R$^5$ have the abovementioned meaning, R$^6$ represents a C$_1$ to C$_4$ alkyl
or a ketal of the general formula IV
in which

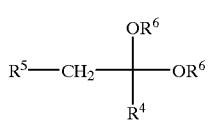

R$^4$, R$^5$ and R$^6$ have the abovementioned meaning at temperatures of 40 to 200° C. without a solvent or in an inert organic solvent in the atmosphere or under a pressure of up to 100 bar, wherein an aliphatic sulfonic acid of the general formula V

    V in which
R$^7$ represents halogen, a branched or unbranched, optionally halogen-substituted alkyl having 1 to 20 C atoms or a cycloalkyl,
or a sulfonic acid salt of the general formula VI

    VI in which
R$^8$=R$^7$ and additionally represents an aryl or a substituted aryl and
M represents a cation of an organic or inorganic base, is used as the process catalyst.

2. Process for the preparation of an unsaturated 3,5-diene ketone and the corresponding saturated ketones by isomerization of an 4,5-allene ketone or hydrogenation of a 4,5-allene ketone of the formula I

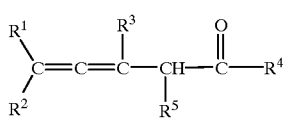

in which
R$^1$ and R$^2$ represent a hydrogen, a saturated or unsaturated, branched or unbranched C$_1$ to C$_{20}$-alkyl, aryl or alkylaryl, R$^1$ and R$^2$ together to form a 5- or 6-membered ring, $R^3$ and $R^5$ represent hydrogen or a $C_1$ to $C_4$-alkyl and $R^4$ represents a $C_1$ to $C_4$ alkyl, by reacting a tertiary propargyl alcohol of the general formula II

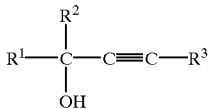

II in which $R^1$, $R^2$ and $R^3$ have the abovementioned meaning, with an alkenyl alkyl ether of the general formula III

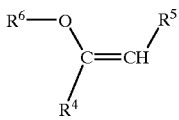

III in which $R^4$, $R^5$ have the abovementioned meaning, $R^6$ represents a $C_1$ to $C_4$ alkyl or a ketal of the general formula IV

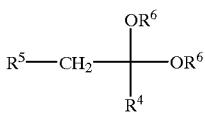

IV in which $R^4$, $R^5$ and $R^6$ have the abovementioned meaning at temperatures of 40 to 200° C. without a solvent or in an inert organic solvent in the atmosphere or under a pressure of up to 100 bar, wherein an aliphatic sulfonic acid of the general formula V $R^7SO_3H$  V in which $R^7$ represents halogen, a branched or unbranched, optionally halogen-substituted alkyl having 1 to 20 C atoms or a cycloalkyl, or a sulfonic acid salt of the general formula VI $R^8SO_3M$  VI in which $R^8$=$R^7$ and additionally represents an aryl or a substituted aryl and M represents a cation of an organic or inorganic base, is used as the process catalyst.

3. The process according to claim 1, wherein the 4,5-allene ketone of the formula I denotes a member selected from the group consisting of 6,10-dimethyl-4,5-undecadien-2-one, 6-methyl-4,5-heptadien-2-one, 6,10-dimethyl-4,5,9-undecatrien-2-one, 6,10,14-trimethyl-4,5,9,13-pentadecatetraen-2-ones and 6,10,14-trimethyl-4,5-pentadecadien-2-one.

4. The process according to claim 2, wherein the 4,5-allene ketone of the general formula I is prepared in situ and is converted into methylheptanone, tetrahydrogeranylacetone, pseudoionone or phytone by isomerization or hydrogenation.

5. The process according to claim 1, wherein the aliphatic sulfonic acid of the formula V denotes a member selected from the group consisting of methane-, ethane-, propane-, butane-, pentane-, hexane-, halogen-substituted methane- and cyclohexanesulfonic acid.

6. The process according to claim 1, wherein the sulfonic acid salt of the formula VI denotes a member selected from the group consisting of pyridinium p-toluenesulfonate, tetramethylammonium p-toluenesulfonate, pyridinium methanesulfonate, and pyridinium ethanesulfonate.

7. The process according to claim 1, wherein the preparation of the 4,5-allene ketone of the formula I is carried out at a temperature of from 50° C. and 120° C., under a pressure of from 1 to 20 bar.

8. The process according to claim 1, wherein the preparation of the 4,5-allene ketone of the formula I is carried out in an organic hydrocarbon, aromatic, ketone or ether as the solvent.

9. The process according to claim 1, wherein the ratio of the tertiary alcohol of formula II and the alkyl ether of formula III is from 1:2 to 1:10.

* * * * *